(12) United States Patent
Stelter

(10) Patent No.: US 11,491,031 B2
(45) Date of Patent: Nov. 8, 2022

(54) METHOD FOR MANUFACTURING A BREAST PROSTHESIS

(71) Applicant: Amoena Medizin-Orthopädie-Technik GmbH, Raubling (DE)

(72) Inventor: Nils Stelter, Frasdorf (DE)

(73) Assignee: Amoena Medizin-Orthopädie-Technik GmbH, Raubling (DE)

( * ) Notice: Subject to any disclaimer, the term of this patent is extended or adjusted under 35 U.S.C. 154(b) by 317 days.

(21) Appl. No.: 16/568,447

(22) Filed: Sep. 12, 2019

(65) Prior Publication Data
US 2020/0085594 A1 Mar. 19, 2020

(30) Foreign Application Priority Data
Sep. 14, 2018 (DE) ...................... 10 2018 122 566.0

(51) Int. Cl.
*B29C 61/02* (2006.01)
*A61F 2/50* (2006.01)
*A61F 2/52* (2006.01)
*B29C 61/00* (2006.01)
*B29C 67/20* (2006.01)
*B29K 83/00* (2006.01)
*B29K 101/12* (2006.01)
*B29K 105/04* (2006.01)
*B29K 105/00* (2006.01)
*B29L 31/00* (2006.01)
*C08J 9/26* (2006.01)

(52) U.S. Cl.
CPC ............. *A61F 2/5044* (2013.01); *A61F 2/52* (2013.01); *B29C 61/003* (2013.01); *B29C 61/02* (2013.01); *B29C 67/202* (2013.01); *A61F 2002/5053* (2013.01); *A61F 2002/5055* (2013.01); *A61F 2002/526* (2013.01); *B29K 2083/00* (2013.01); *B29K 2101/12* (2013.01); *B29K 2105/04* (2013.01); *B29K 2105/251* (2013.01); *B29L 2031/7532* (2013.01); *C08J 9/26* (2013.01)

(58) Field of Classification Search
CPC ..... B29C 61/003; B29C 61/02; A61F 2/5044; A61F 2002/5053; B29K 2083/00; B29K 2101/12; B29K 2105/04; B29K 2105/251; B29L 2031/7532
USPC ........................................................ 264/308
See application file for complete search history.

(56) References Cited

U.S. PATENT DOCUMENTS 5,340,352 A * 8/1994 Nakanishi ............. B29C 67/202
                                                        450/55
5,733,335 A * 3/1998 Ishikawa ................... A61F 2/52
                                                        623/7

(Continued)

FOREIGN PATENT DOCUMENTS

CN       105034395 A      11/2015
CN       108289744 A       7/2018

(Continued)

*Primary Examiner* — Christina A Johnson
*Assistant Examiner* — Xue H Liu
(74) *Attorney, Agent, or Firm* — Dilworth & Barrese, LLP

(57) ABSTRACT

The invention relates to a method for manufacturing a breast prosthesis, in which a first dispersion of a first granular material is introduced into a cross-linkable silicone compound. The silicone compound subsequently is cured in order to form a prosthesis body, wherein the prosthesis body is heated to a shrinking temperature which lies above the melting point of the thermoplastic material.

19 Claims, 4 Drawing Sheets

(56) References Cited

U.S. PATENT DOCUMENTS

| | | | |
|---|---|---|---|
| 6,296,800 B1* | 10/2001 | Stelter .................. | B29C 70/603 |
| | | | 264/320 |
| 2010/0256777 A1 | 10/2010 | Datta | |
| 2012/0077010 A1* | 3/2012 | Manesis .................... | B32B 5/26 |
| | | | 428/220 |
| 2013/0116786 A1* | 5/2013 | Sanabria Scharf ....... | A61F 2/12 |
| | | | 623/8 |
| 2017/0367850 A1 | 12/2017 | Halley et al. | |

FOREIGN PATENT DOCUMENTS

| | | |
|---|---|---|
| JP | 2004-83876 A | 3/2004 |
| WO | 2013/091720 A1 | 6/2013 |

* cited by examiner

METHOD FOR MANUFACTURING A BREAST PROSTHESIS

BACKGROUND OF THE INVENTION

This invention relates to a method for manufacturing a breast prosthesis and to a breast prosthesis manufactured by the method.

Breast prostheses are worn after mastectomies. Requirements for the breast prostheses in particular comprise a shape and feel coming as close as possible to the natural breast as well as a high wear comfort and good ventilation including a heat regulation of the often scarred skin areas in contact therewith.

For manufacturing such breast prostheses it is known for example from WO 2013/091720 A1 to manufacture a breast prosthesis in that a casting mold including a cavity complementary in shape to the front side of a breast is provided, that a cross-linkable silicone compound is poured into the cavity, brought into layer form and cured in order to obtain a thin skin layer of the breast prosthesis, that the cavity covered by the skin layer is at least partly filled with a dispersion of granular, soluble material in a cross-linkable silicone compound and that the silicone compound is cured, and that the granular, soluble material is removed in order to obtain a prosthesis body with a cellular structure. US 2017/367850 A1 discloses a refined method of this kind, wherein a suspended phase-change material is added to the crosslinkable silicone compound, whose melting point lies in a range slightly below the body temperature.

A disadvantage of these known methods consists in that for removing the granular, soluble material from the cured silicone matrix a dense sphere packing is required, so that all spheres are in contact with each other, in order to ensure washout channels through the entire volume. The pore volume of the prosthesis core thus cannot be chosen freely. The pore homogeneity and the adjustability of the pore size also are not always optimal, and washing out is time-consuming. Residues of the soluble material can hardly be avoided.

SUMMARY OF THE INVENTION

It is the object of the invention to provide a generic method for manufacturing a breast prosthesis, which overcomes the above-mentioned disadvantages.

Against this background, the invention relates to a method for manufacturing a breast prosthesis, comprising the following steps: (b) introducing a first dispersion of first granular material in a cross-linkable silicone compound into a cavity of a casting mold, wherein the first granular material is a porous and preferably foamed thermoplastic material; (d) curing of the silicone compound in order to form a prosthesis body; and (f) heating of the prosthesis body to a shrinking temperature which lies above the melting point of the thermoplastic material.

For pore formation, porous plastic granulate made of a thermoplastic material hence is used according to the invention, which has a lower melting point than the silicone matrix. The porous granulate thereby can be molten, wherein the grains collapse with the escape of the gas enclosed in the pores. There are obtained cavities which render the base material significantly softer, as no more back pressure acts from the wall of the plastic granulate. This method does not require an openpore structure and a dense sphere packing. Rather, the porosity of the silicone matrix and hence the desired weight saving can steplessly be adjusted in a range from 0% to about 50%.

In one embodiment it is provided that the plastic material is expanded polystyrene, expanded polyethylene or expanded polypropylene. Expanded polystyrene (EPS) is particularly preferred.

The porosity of the plastic material can be greater than 0.8 or greater than 0.9. The greater the porosity, the stronger the decrease in volume on melting. The porosity of expanded polystyrene often lies within these ranges.

Preferably, the granular material is at least largely spherical. The first granular material can have a homogeneous particle size distribution, wherein the particle diameter of more than 70% and preferably of more than 85% of the particles deviates from the average particle diameter by less than 10%. In this connection, particle diameter is understood to be the volume-equivalent sphere diameter.

In one embodiment it is provided that the plastic material has a melting point of 120-180° C. Correspondingly, the shrinking temperature can lie between about 140-200° C.

In one embodiment it is provided that the method furthermore comprises the following step preceding step (b): (a) manufacturing a skin layer of the breast prosthesis, wherein a cross-linkable silicone compound is poured into the cavity, brought into layer form and cured. The layer thickness of the skin layer for example can be 2-6 mm, preferably 3-5 mm. The first dispersion then is introduced into the cavity already covered by the skin layer. The skin layer preferably comprises no dispersed particles at all or at least no dispersed particles made of a foamed thermoplastic material.

In one embodiment it is provided that the method furthermore comprises the following step carried out between steps (b) and (d): (c) manufacturing a pore-free terminal zone of the prosthesis body.

Preferably, it is provided that a countermold is placed onto the first dispersion present in the cavity in order to fix the same in its shape, and the casting mold subsequently is supported and the silicone compound is cured with the casting mold turned upside down. By turning the mold upside down the first granular material, which has a lower density than the silicone compound, rises to the front side of the casting mold now lying at the top, so that in the rear end region of the first dispersion, which now lies at the bottom, a terminal zone is formed, which contains the silicone compound of the first dispersion without the dispersed first granular material.

Alternatively, a pore-free terminal zone can be effected for example by applying a higher-viscosity silicone compound onto the back of the prosthesis body to be cured or by filling a low-viscosity silicone compound into a gap between the prosthesis body to be cured and a countermold.

In one embodiment it is provided that the method furthermore comprises the following step carried out between steps (d) and (f): (e) manufacturing a contact layer of the breast prosthesis, wherein a second dispersion of a second granular material in a cross-linkable silicone compound is introduced into the cavity already containing the prosthesis body such that the back of the prosthesis body is at least partly covered, and the silicone compound of the second dispersion subsequently is cured. Thus, a backside contact layer can be manufactured. By means of a suitable procedure, a defined open porosity can be achieved. For example, the contact layer can be designed with openings facing the carrier, in that the casting mold is turned upside down so that the spheres rise to the surface, or the sphere packing can be so dense that the granulate breaks through to the surface. As a result, a ventilating surface structure is formed, which generates an optimized microclimate. The backside layer should be chosen so thick that a good ventilation is obtained, but so thin that it can dry well after cleaning.

Due to a pore-free terminal zone of the prosthesis body, impurities cannot penetrate into the prosthesis body.

The second granular material likewise can be a foamed thermoplastic material whose melting point lies below the shrinking temperature. In one embodiment it is provided that the first granular material of the first dispersion and the second granular material of the second dispersion consist of the same plastic material. This facilitates the procedure, all the more so as in this case the optimum shrinking temperature is the same for both plastic materials. It can be provided that the material of the first and the second granulate generally is the same, i.e. also has the same porosity etc.

Alternatively, the second granular material can also comprise a soluble material such as for example sugar. This material preferably is washed out before heating in step (f) in order to prevent chemical changes, in the case of sugar for example a caramelization.

In one embodiment it is provided that the average particle diameter of the second granular material is greater than the average particle diameter of the first granular material. It can be provided to aim at larger pores for the contact layer, as this can lead to a softer mass and better ventilation.

The silicone compound used in steps (a), (b) and (e) can chemically correspond to each other. Suitable silicone compounds for each of the steps comprise addition cross-linking two-component silicone rubber compounds. Curing by cross-linking generally can be effected at room temperature or also at higher temperatures.

To the silicone compound for forming the pore-free terminal zone or, in the case of the presence of step (e), of the second dispersion a phase-change material possibly can be added, whose phase transition temperature is close to the body temperature. Suitable examples comprise paraffins with a suitable number of carbon atoms, typically about twenty, in order to adjust a melting point in the desired range. By adding the phase-change material especially to the silicone compound for forming the pore-free terminal zone or second dispersion, from which the layer close to the body results, the phase-change material acts where its action is needed, namely directly at the body of the wearer.

The invention furthermore relates to a breast prosthesis with a porous prosthesis body, wherein the prosthesis is manufactured by a method according to the invention. Due to the type of manufacture, the prosthesis body includes residues of a molten thermoplastic material in its pores. These residues however have no perceptible influence on the haptic properties of the prosthesis.

Preferred embodiments of the prosthesis can be taken from the aspects described in connection with the method of the invention. In particular, when the method comprises a preceding step (a), the prosthesis can include a layer, preferably skin layer, adjoining the front side of the prosthesis body. Furthermore, when the method comprises an intermediate step (c), the prosthesis can include a pore-free backside terminal zone of the prosthesis body. Furthermore, when the method comprises an intermediate step (e), the prosthesis can include a porous contact layer on the back of the prosthesis body. It is preferred particularly when the prosthesis includes all of these layers.

BRIEF DESCRIPTION OF THE DRAWINGS

Further details and advantages of the invention can be taken from the exemplary embodiment described below with reference to the Figures. In the Figures:

FIG. 5: shows the casting mold of FIG. 4 with a first dispersion poured in; and

FIG. 6: shows the casting mold of FIG. 5 with a second dispersion poured in.

DESCRIPTION OF THE PREFERRED EMBODIMENTS

Figure 1:
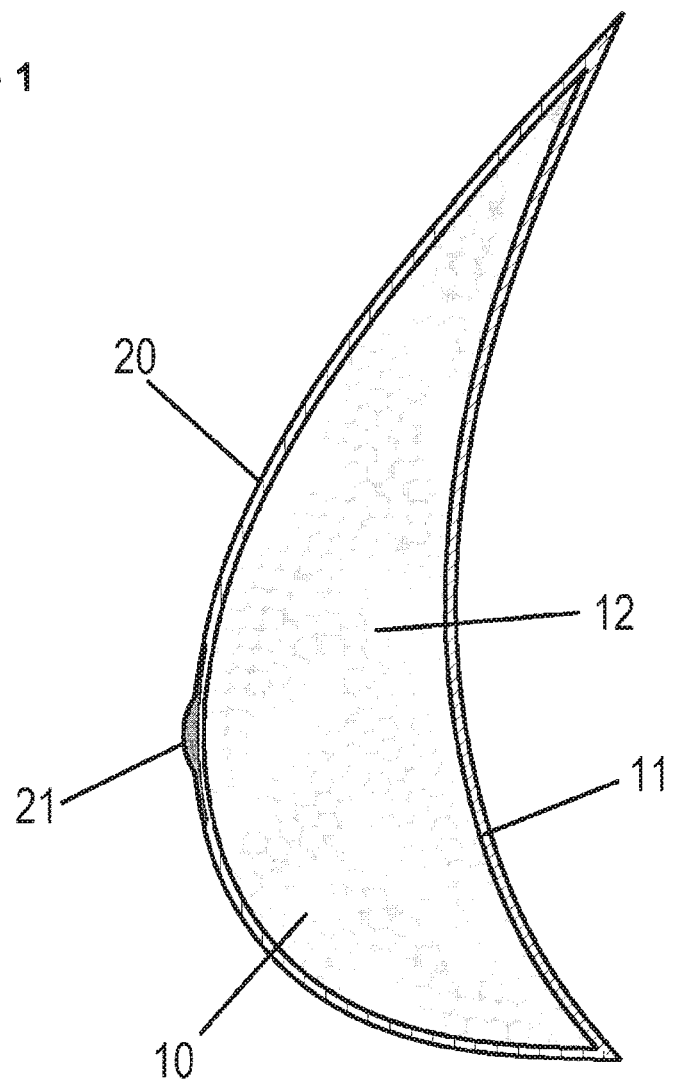
FIG. 1: shows an embodiment of a breast prosthesis according to the invention.
Figure 2:
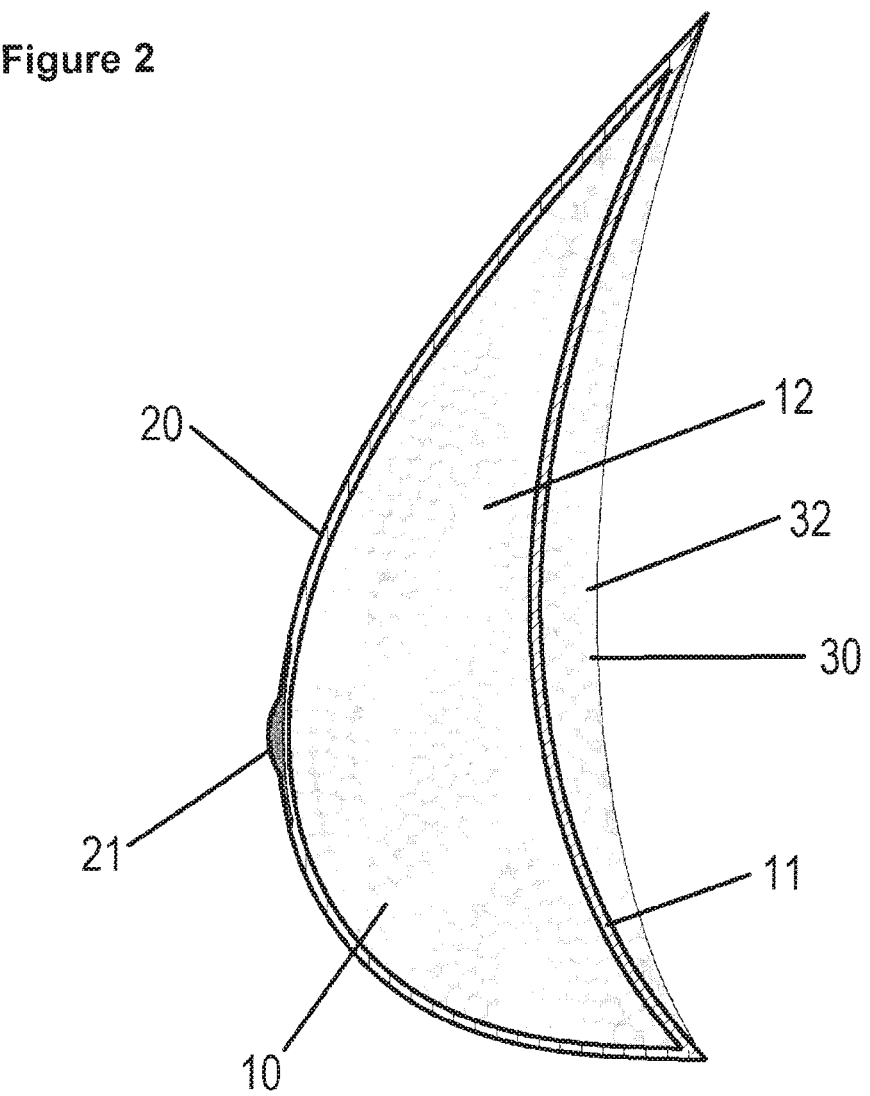
FIG. 2: shows another embodiment of a breast prosthesis according to the invention.

FIGS. 1-2 show two different embodiments of breast prostheses according to the invention. Both prostheses comprise a porous prosthesis body 10 which on its front side has a pore-free skin layer 20 and on its back a pore-free terminal zone 11. On the front side of the skin layer 20 a nipple imitation 21 furthermore is mounted. The layers 10 and 20 as well as preferably also the nipple imitation 21 are fabricated from silicone rubber.

The breast prosthesis shown in FIG. 21 additionally comprises a porous contact layer 30 which adjoins the back of the prosthesis body 10. All layers 10, 20 and 30 as well as preferably also the nipple imitation 21 are fabricated from silicone rubber, wherein the layers 10 and 30 have a different porosity and different pore structures.

The pores 32 of the porous contact layer 30 are larger than the pores 12 of the prosthesis body 10. Furthermore, the pore structure of the porous contact layer 30 is open-pored with a high porosity close to the space filling degree of a densest sphere packing, while the prosthesis body 10 has a closed-pore structure with lower porosity.

Due to a pore-free terminal zone 11 of the prosthesis body 10, impurities cannot advance from the contact layer 30 into the prosthesis body 10.

With reference to FIGS. 3-6 a method for manufacturing the illustrated prostheses according to the invention can be explained.

Figure 3:
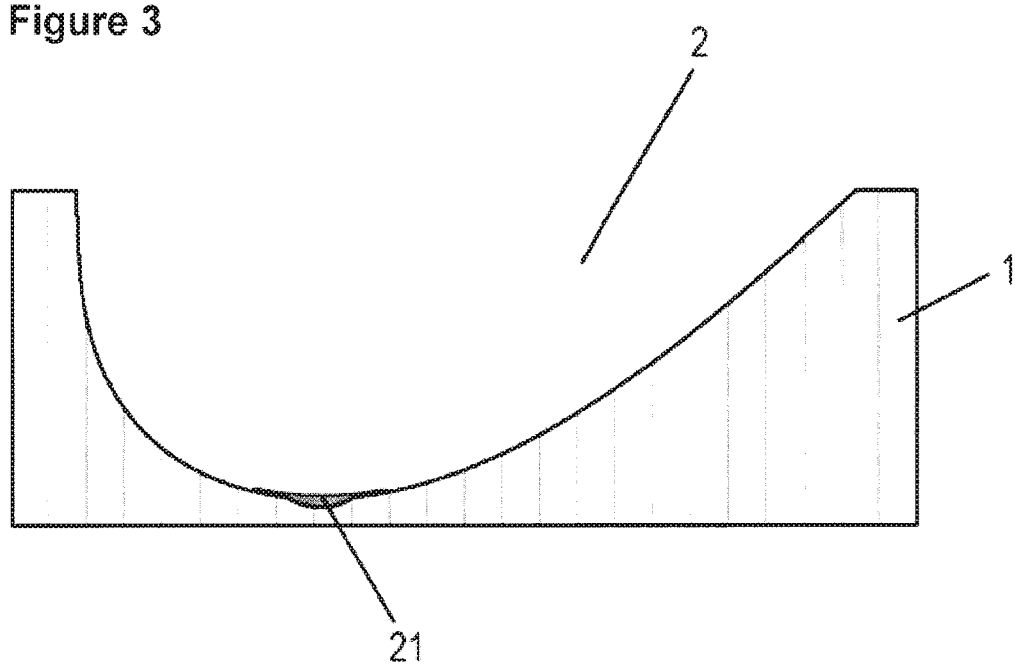
FIG. 3: shows a casting mold for manufacturing a breast prosthesis according to the invention with a nipple imitation inserted into the cavity.

The casting mold 1 shown in FIG. 3 includes a cavity 2 which is shaped corresponding to a female breast. The casting mold 1 typically is manufactured from a temperature-resistant material. The shape of the cavity 2 can be custom-made or suitable for series production. The nipple imitation 21 is inserted into the cavity 2 at a corresponding point. The imitation 21 can be fabricated from an especially colored silicone rubber. The softness likewise can deviate from the remaining silicone. A useful silicone for example is Silpuran® 2420 of the firm Wacker-Chemie. The nipple imitation 11 can be fabricated by introducing a curable silicone compound into the cavity 2 and curing the same. The corresponding area can be delimited by a plastic ring temporarily inserted into the cavity 2. Cross-linking can be effected at room temperature or also at higher temperatures.

Figure 4:
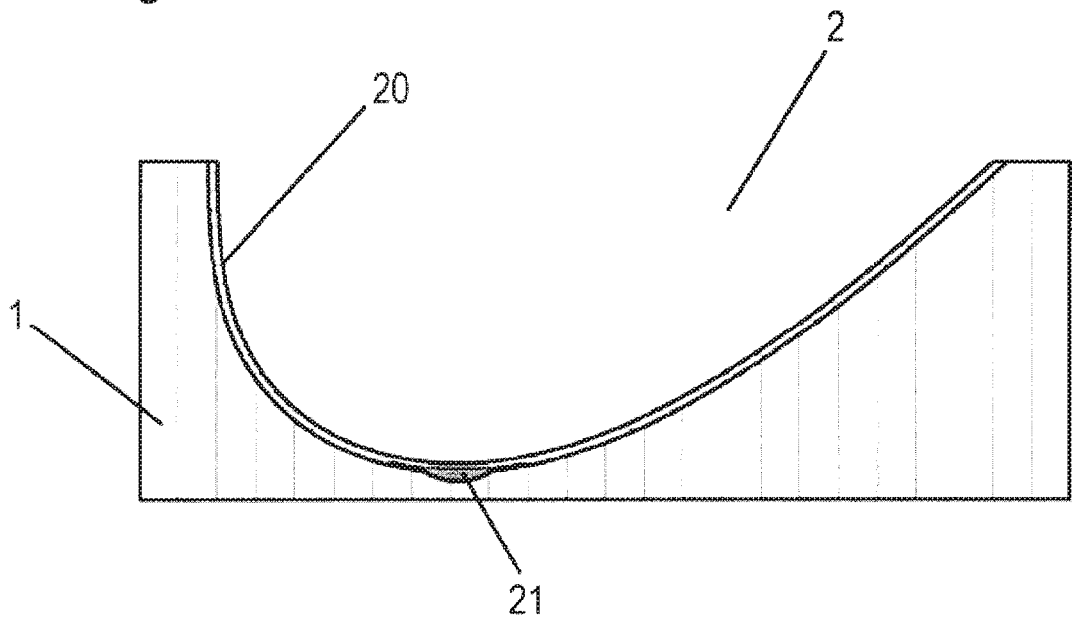
FIG. 4: shows the casting mold of FIG. 3 with a skin layer covering the cavity.

Next, the skin layer 20 is fabricated, as can be seen in FIG. 4. For this purpose, a cross-linkable silicone compound is filled into the open cavity 2 and the same subsequently is closed with a non-illustrated counterpart in order to produce the skin layer 20 having a thickness of 2-3 mm by subsequent cross-linkage. Alternatively, the silicone compound can be pressed into the cavity 2 closed already with the counterpart. Cross-linking in turn can be effected at room temperature or also at higher temperatures.

Figure 5:
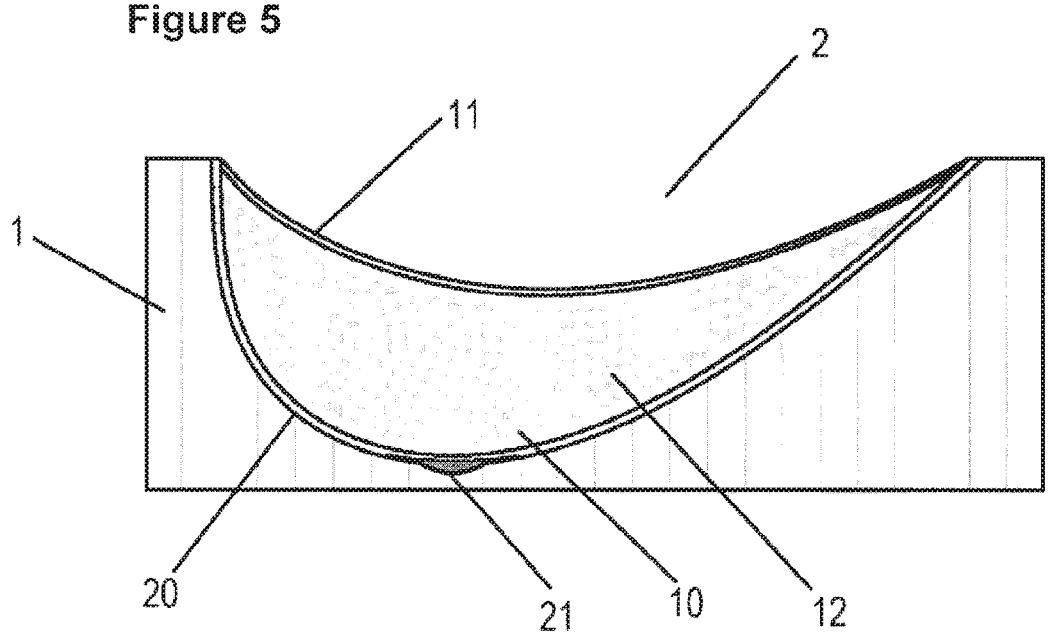

Subsequently, as shown in FIG. 5, a first dispersion comprising expanded polystyrene (EPS) spheres with an average particle diameter of 1-2 mm, which are dispersed in a cross-linkable silicone compound, is filled into the open cavity 2. The cavity 2 then is closed with a non-illustrated counterpart and the silicone compound is cross-linked.

The enriched silicone compound is coated with another, thin silicone layer having a thickness of about 1-2 mm, in order to form the pore-free terminal zone 11. This can be effected for example by applying a higher-viscosity silicone compound onto the back of the prosthesis body to be cured or by filling a low-viscosity silicone compound into a gap between the prosthesis body to be cured and the counterpart.

Figure 6:
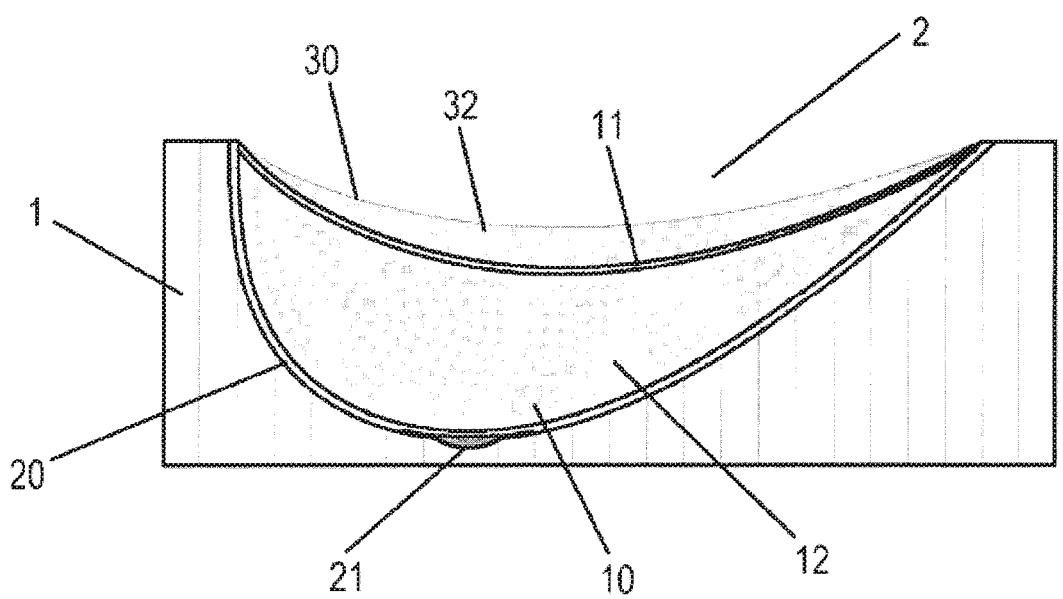

In the variant of FIG. 2 another layer is applied, as can be seen in FIG. 6. This layer results in the porous contact layer 30 which adjoins the back of the prosthesis body 10. Namely, a second dispersion comprising expanded polystyrene (EPS) spheres with an average particle diameter of more than 2 mm, which are dispersed in a cross-linkable silicone compound, is filled into the open cavity 2 and crosslinked.

To the second dispersion, a paraffin with an average carbon number of about twenty is added in addition, whose phase transition temperature is close to the body temperature. By adding the phase-change material especially to the second dispersion, from which the porous contact layer 30 results, the phase-change material acts where its action is needed, namely directly at the body of the wearer.

The molded parts on the back can be adjusted to the scar contour of the female customer, in case it is no series tool.

Finally, the molded part on the back is removed. The shrinkback of the plastic spheres is effected at about 150-180° C. for about 2 h. Either the mold 1 together with the prosthesis is heated or the silicone prosthesis first is removed from the mold. Heating in the mold 1 has proved its worth, as the difficult removal of the yet compact prosthesis from the mold is omitted.

As the silicone surface can be slightly tacky, which can render insertion into the bra pocket considerably more difficult, the silicone surface is also treated with a Low Friction Silicone Coating MED10-6670 of the firm NuSil.

The invention claimed is:

1. A method for manufacturing a breast prosthesis, comprising the following steps:
   (b) introducing a first dispersion of a first granular material in a cross-linkable silicone compound into a cavity of a casting mold, wherein the first granular material is a porous thermoplastic material;
   (d) curing of the silicone compound to form a prosthesis body; and
   (f) heating of the prosthesis body to a shrinking temperature which lies above the melting point of the thermoplastic material.

2. The method according to claim 1, wherein the plastic material is expanded polystyrene, expanded polyethylene or expanded polypropylene.

3. The method according to claim 1, wherein the plastic material has a melting point of 120-180° C. and the shrinking temperature lies between 140-200° C.

4. The method according to claim 1, wherein the method furthermore comprises the following step preceding step (b):
   (a) manufacturing a skin layer of the breast prosthesis, wherein a cross-linkable silicone compound is poured into the cavity, brought into layer form and cured.

5. The method according to claim 1, wherein the method furthermore comprises the following step carried out between steps (b) and (d):
   (c) manufacturing a pore-free terminal zone of the prosthesis body.

6. The method according to claim 1, wherein the method furthermore comprises the following step carried out between steps (d) and (f):
   (e) manufacturing a contact layer of the breast prosthesis, wherein a second dispersion of second granular material in a cross-linkable silicone compound is introduced into the cavity already containing the prosthesis body such that the back of the prosthesis body is at least partly covered, and the silicone compound of the second dispersion subsequently is cured.

7. The method according to claim 6, wherein the second granular material also is a foamed thermoplastic material whose melting point lies below the shrinking temperature.

8. The method according to claim 6, wherein the average particle diameter of the second granular material is greater than the average particle diameter of the first granular material.

9. The method according to claim 5, wherein a phase-change material is introduced into the pore-free terminal zone and/or a contact layer.

10. The method according to claim 1, wherein the plastic material has a melting point of 120-180° C. and the shrinking temperature lies between 140-200° C.

11. The method according to claim 10, wherein the method furthermore comprises the following step preceding step (b):
   (a) manufacturing a skin layer of the breast prosthesis, wherein a cross-linkable silicone compound is poured into the cavity, brought into layer form and cured.

12. The method according to claim 3, wherein the method furthermore comprises the following step preceding step (b):
   (a) manufacturing a skin layer of the breast prosthesis, wherein a cross-linkable silicone compound is poured into the cavity, brought into layer form and cured.

13. The method according to claim 2, wherein the method furthermore comprises the following step preceding step (b):
   (a) manufacturing a skin layer of the breast prosthesis, wherein a cross-linkable silicone compound is poured into the cavity, brought into layer form and cured.

14. The method according to claim 13, wherein the method furthermore comprises the following step carried out between steps (b) and (d):
   (c) manufacturing a pore-free terminal zone of the prosthesis body.

15. The method according to claim 12, wherein the method furthermore comprises the following step carried out between steps (b) and (d):
   (c) manufacturing a pore-free terminal zone of the prosthesis body.

16. The method according to claim 11, wherein the method furthermore comprises the following step carried out between steps (b) and (d):
   (c) manufacturing a pore-free terminal zone of the prosthesis body.

17. The method according to claim 10, wherein the method furthermore comprises the following step carried out between steps (b) and (d):
   (c) manufacturing a pore-free terminal zone of the prosthesis body.

18. The method according to claim 4, wherein the method furthermore comprises the following step carried out between steps (b) and (d):
   (c) manufacturing a pore-free terminal zone of the prosthesis body.

19. The method according to claim 1, wherein the first granular material is a foamed thermoplastic material.

* * * * *